United States Patent [19]

Schwarzmaier et al.

[11] Patent Number: 5,507,920
[45] Date of Patent: Apr. 16, 1996

[54] PROCESS AND APPARATUS FOR PURIFYING VINYL CHLORIDE

[75] Inventors: Peter Schwarzmaier, Kastl; Peter Kammerhofer, Burgkirchen; Manfred Stöger, Burgkirchen; Helmut Kalliwoda, Burgkirchen; Ingolf Mielke, Burgkirchen, all of Germany

[73] Assignee: Hoechst Aktiengesellschaft, Germany

[21] Appl. No.: 350,626

[22] Filed: Dec. 7, 1994

[30] Foreign Application Priority Data

Dec. 9, 1993 [DE] Germany .................. 43 42 042.7

[51] Int. Cl.$^6$ .................................................. B01D 15/00
[52] U.S. Cl. .................... 203/41; 23/14; 23/71; 23/73
[58] Field of Search ................... 203/14, 71, 73, 203/80, 41; 570/262, 226, 238

[56] References Cited

U.S. PATENT DOCUMENTS

| | | | |
|---|---|---|---|
| 3,476,955 | 11/1969 | Krekeler et al. | 570/226 |
| 3,761,361 | 9/1973 | Wall | 570/226 |
| 3,843,736 | 10/1974 | Rechmeier et al. | |
| 3,963,584 | 6/1976 | Tsao | 570/262 |
| 4,642,400 | 2/1987 | Cowfer et al. | 570/226 |
| 4,769,112 | 9/1988 | Wheldon | 203/41 |

FOREIGN PATENT DOCUMENTS 3024156  1/1982  Germany .

*Primary Examiner*—Timothy M. McMahon
*Attorney, Agent, or Firm*—Connolly & Hutz

[57] ABSTRACT

In the preparation of vinyl chloride by thermal cracking of 1,2-dichloroethane, three distillation stages are used to distill off first hydrogen chloride, then vinyl chloride and finally entrained hydrogen chloride with vinyl chloride. If, in the last stage, entrained water is not drawn off via the bottom, it is recirculated with the top product to the first stage and causes corrosion. Removal of the water at the top of the third distillation stage, advantageously by drying, prevents the corrosion.

4 Claims, 1 Drawing Sheet

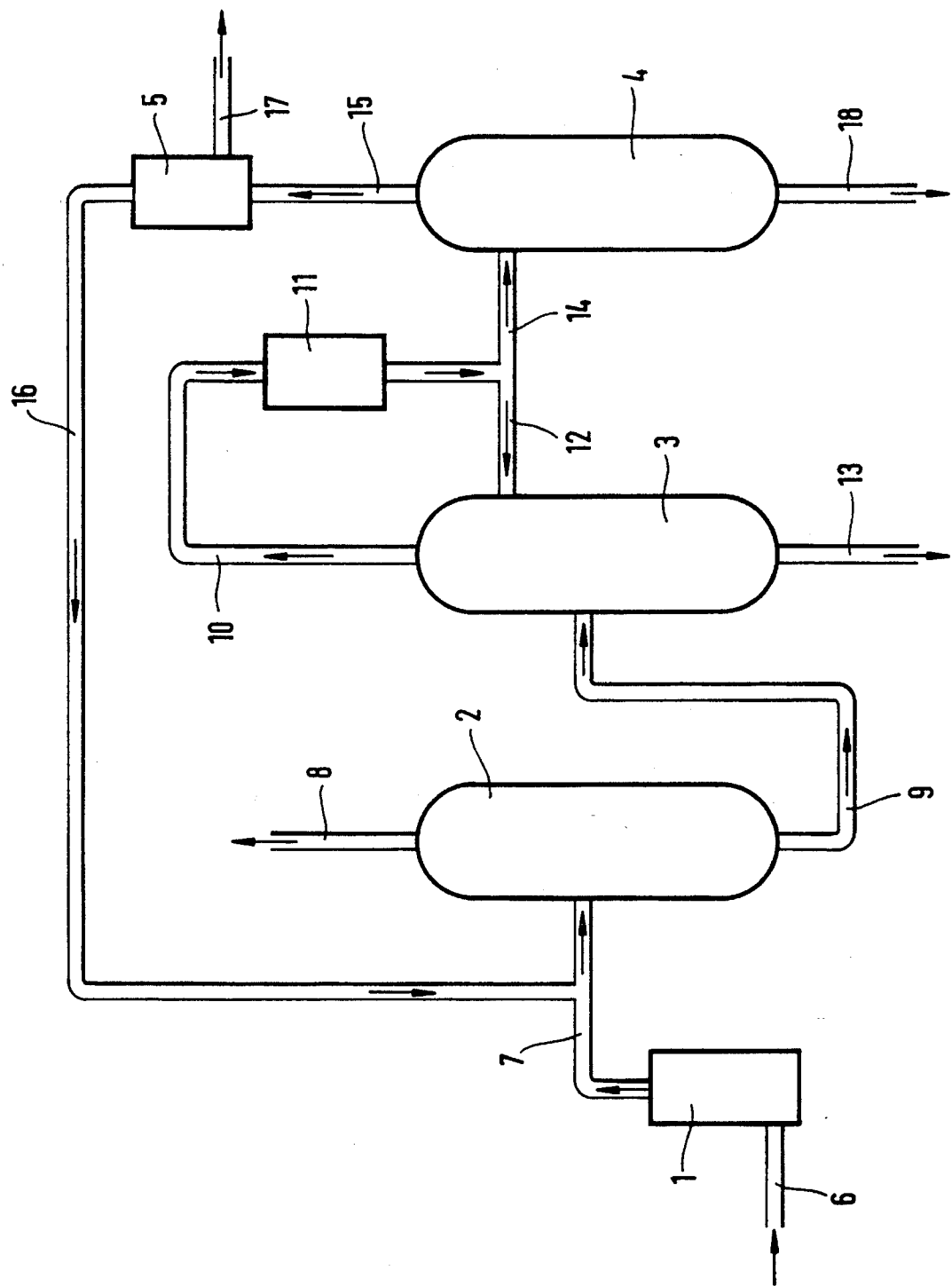

PROCESS AND APPARATUS FOR PURIFYING VINYL CHLORIDE

BACKGROUND OF THE INVENTION

U.S. Pat. No. 3 843 736 discloses a process for isolating vinyl chloride from the reaction mixture obtained in the incomplete thermal cracking of 1,2-dichloroethane at a superatmospheric pressure of preferably from 8 to 40 atm. absolute and temperatures between about 450° and 650° C. in the absence of catalysts, with the gas mixture leaving the cracking zone, comprising vinyl chloride, hydrogen chloride, unreacted 1,2-dichloroethane and byproducts, being conveyed in partially condensed form into a first distillation stage to distill off the hydrogen chloride and subsequently being conveyed into a second distillation stage to distill off the vinyl chloride, the bottom product of the second distillation stage then being worked up in a known manner for the purpose of recycling the unreacted 1,2-dichloroethane, and with the vinyl chloride drawn off at the top of the second distillation stage and liquefied being partially pumped back into about the middle of the first distillation stage, in which process the vinyl chloride drawn off and liquefied as product, which still contains small amounts of hydrogen chloride, is fed to the top of a degassing zone from which a part of the vinyl chloride is evaporated by means of a circulation evaporator together with the entire entrained hydrogen chloride, the evaporated vinyl chloride is condensed and pumped back into about the middle of the first distillation stage provided for distilling off the hydrogen chloride, while very pure vinyl chloride is taken off from the bottom of the degassing zone.

This patent also mentions that the small amounts of hydrogen chloride which are removed in the degassing zone were formerly separated off by means of towers filled with sodium hydroxide.

However, the known process is disadvantageous if the vinyl chloride fed to the degassing zone still contains small amounts of water. These are unavoidable in practice; especially when running up the plant and during interruptions in operation, traces of water are unavoidably introduced. In practice, therefore, the degassing zone was then operated in such a way that these amounts of water were separated off via the bottom of the degassing column, together with hydrogen chloride, for which purpose the towers filled with sodium hydroxide were again required. If this separation of the water were not carried out via the bottom of the degassing column, the water would be circulated together with the recycled vinyl chloride and lead to corrosion in the affected parts of the plant. However, such corrosion is unacceptable not only for economic reasons, but especially for safety reasons.

SUMMARY OF THE INVENTION

It has now been found that the towers filled with sodium hydroxide can be omitted if the degassing column is operated in such a way that the major part of the water is taken off at the top and removed, advantageously by drying. The dry, hydrogen chloride-containing vinyl chloride recirculated to the process can no longer cause corrosion.

BRIEF DESCRIPTION OF THE DRAWING

The single FIGURE of drawing is a diagrammatical view of apparatus for purifying vinyl chloride, according to the present invention.

DETAILED DESCRIPTION OF THE INVENTION

The invention accordingly provides a process for isolating vinyl chloride, which comprises distilling off the hydrogen chloride from the reaction mixture formed in the incomplete thermal cracking of 1,2-dichloroethane at superatmospheric pressure and temperatures of from about 450° to about 650° C. in the absence of catalysts in a first distillation stage and distilling off the vinyl chloride in a second distillation stage, with the vinyl chloride drawn off at the top of the second distillation stage and liquefied being partially recirculated as runback into the second distillation stage and the remaining liquefied vinyl chloride drawn off being fed to the top of a degassing zone from which a part of the vinyl chloride together with the entire entrained hydrogen chloride and water is evaporated and, after substantial removal of the water, recirculated into the first distillation stage, while pure vinyl chloride is taken off from the bottom of the degassing zone.

The invention further provides an apparatus for preparing vinyl chloride having a cracking zone (1), a first distillation stage (2) for separating off hydrogen chloride, a second distillation stage (3) for distilling off vinyl chloride from higher-boiling constituents and a third distillation stage (4) for separating off hydrogen chloride and water from the vinyl chloride, which comprises an apparatus (5) (drying zone) via which the hydrogen chloride and water separated off in the third distillation stage (4) are recirculated together with vinyl chloride to the first distillation stage (2) and in which the water is substantially removed.

The apparatus of the invention is schematically shown in the figure. Besides the apparatus (1) to (5) already mentioned, this includes:

(6) the feed line for 1,2-dichloroethane to the cracking zone (1), (7) a line for the cracking products to the first distillation stage (2), (8) a line for the hydrogen chloride separated off, (9) a line for the higher-boiling products to the second distillation stage (3),

(10) a line to a condenser (11) for the liquefaction of the vinyl chloride,

(12) a line for a substream of the liquefied vinyl chloride back to the second distillation stage (3),

(13) a line for separating off high-boiling byproducts,

(14) a line for a second substream of the liquefied vinyl chloride to the third distillation stage (4),

(15) a line from the third distillation stage (4) to the drying zone (5),

(16) a line for the dried mixture comprising hydrogen chloride and residual vinyl chloride back to the first distillation stage (2),

(17) a line for the water separated off and

(18) a line for the pure vinyl chloride.

In the separation of the water according to the invention, a highly corrosive mixture of vinyl chloride, hydrogen chloride and water enters the drying zone. It is known that under such circumstances polymerization of the vinyl chloride can occur (catalysis by traces of metals). Surprisingly, however, even on prolonged operation in metal apparatus, no deposit of polyvinyl chloride could be found.

The substantial removal of the water according to the invention can be carried out in the manner known for acid fluids. This can be carried out by condensation of the water, but preferably by drying, for example using agents which undergo chemical transformation, for example liquid desiccants such as concentrated sulfuric acid or solid desiccants such as phosphorus pentoxide or calcium chloride. Preference is given to desiccants which retain the water adsorptively, such as molecular sieves and, in particular, silica gels.

The drying zone preferably comprises at least two dryers connected in parallel, with the water-containing mixture to be recirculated being conveyed through the one, while the other (or the others) is (are) regenerated or freshly charged. It is naturally also possible to operate a plurality of drying apparatus in series. The materials of value, vinyl chloride and hydrogen chloride, liberated on regeneration can be recirculated to the process.

In a preferred embodiment of the invention, the drying apparatus are configured in such a way that for regeneration they can be heated and flushed with an inert gas such as carbon dioxide, a noble gas or, preferably, nitrogen. Suitable apparatus are, for example, tube heat exchangers or containers having internal coils of tubing.

According to the invention, the gas stream taken off via the top of the degassing column can be dried or the top product can be condensed and the condensate can be conducted through the dryer(s).

It is advantageous to install the dryers as close as possible to the degassing zone, since the greatest water concentration prevails at the top of this column, particularly when the gas phase is to be dried. In this case, the dryer can be installed at the beginning of the vapor line.

Even if, according to the invention, sodium hydroxide towers and the like can be omitted, the invention of course also includes embodiments in which such apparatus are retained, for example for safety reasons. In this case, these apparatus then have considerably higher operating lives and a correspondingly reduced formation of salt and wastewater.

If subsequent treatment with sodium hydroxide or similar-acting agents is omitted, not only are these materials and the apparatus saved, but the expense of servicing and maintenance thereof is also saved. Furthermore, the entire apparatus can then be operated in a closed system. This also eliminates emissions or the facilities used for their prevention during opening, cleaning and charging of these apparatus.

The invention is illustrated by the following examples.

EXAMPLE 1

A vinyl chloride stream of 39 kg/h having an average water content of 29.5 ppm is pumped through a tube (length 200 mm, diameter 80 mm) filled with a wire mesh having a mesh spacing of 125 μm and charged with 740 g of silica gel (commercial "Blaugel", fine-pored, particle size from 1 to 3 mm); the pressure at the inlet of the tube is 16 bar. After a running time of 21 hours, the silica gel has adsorbed 15.45 g of water, corresponding to a loading of 2.1% by weight. The water content in the vinyl chloride flowing out is 7.1 ppm.

For desorption, low-pressure steam is passed through the apparatus. After 180 minutes, the residual loading of the silica gel is <0.3%.

EXAMPLE 2

In a pilot plant, a vinyl chloride stream of 39 kg/h is conveyed through a cylindrical container for 19 hours. Dimensions and charging otherwise correspond to the container described in Example 1. After a running time of 19 hours, the loading of the silica gel is 3.07% by weight. The water content of the dried vinyl chloride is 6.5 ppm.

For regeneration, the container is heated to about 120° C. (internal temperature), with a stream of nitrogen of 100 l/h being passed through the apparatus. After 3 hours, the loading of the silica gel is 0.25%.

EXAMPLE 3

In a pilot plant, a vinyl chloride stream of 34 kg/h having an average water content of 30 ppm is pumped at a pressure of about 16 bar through a tube (length 200 mm, diameter 80 mm) filled with molecular sieve (WESSALITH US 330, Degussa, Hanau). After a running time of 88 hours, the molecular sieve has adsorbed 738 g of water which corresponds to a loading of 31.9% by weight, based on the adsorbent. After desorption for 23 hours at 250° C., the residual loading is about 13% by weight.

EXAMPLE 4

A substream of the top stream from the third distillation stage comprising 0.37 kg of vinyl chloride having a hydrogen chloride content of about 4 g (1,000 ppm) and a water content of about 6 mg (16 ppm) is drawn off in gaseous form and conveyed through a drying apparatus. The drying apparatus comprises a tube having a length of 200 mm and a diameter of 15 mm. It is filled with 35 g of silica gel (commercial "Blaugel", fine-pored, particle size from 1 to 3 mm). After 100 l of the specified gas stream had been conveyed through this dryer, the loading of the desiccant was 12.8% by weight. The gas flowing out had an average water content of 0.5 ppm.

We claim:

1. A process for preparing vinyl chloride comprising the steps of feeding 1,2-dichloroethane into a cracking zone where it is incompletely thermally cracked at superatmospheric pressure and a temperature of from about 450° to about 650° C. in the absence of a catalyst to produce a reaction mixture of vinyl chloride, hydrogen chloride, unreacted 1,2-dichloroethane and high boiling products, passing the reaction mixture into a first distillation stage when most of the hydrogen chloride is distilled off and the higher boiling components are fed into a second distillation stage, distilling off the vinyl chloride in the second distillation stage and removing the higher boiling products, feeding the vinyl chloride distilled off in the second distillation stage into a condenser, liquefying the vinyl chloride in the condenser, splitting the liquefied vinyl chloride into two partial streams, feeding one of the partial streams back into the second distillation stage and the other partial stream into a third distillation stage, distilling off in the third distillation stage a mixture of entrained hydrogen chloride, entrained water and vinyl chloride while removing pure vinyl chloride from the third distillation stage, passing the mixture of entrained hydrogen chloride, entrained water and vinyl chloride into a drying zone, substantially removing the water from the hydrogen chloride and vinyl chloride in the drying zone to produce a dried mixture, and recirculating the dried mixture of hydrogen chloride and vinyl chloride back into the first distillation zone.

2. The process as claimed in claim 1, wherein the removal of the water is carried out with the aid of a desiccant.

3. The process as claimed in claim 2, wherein the desiccant used adsorbs the water.

4. The process as claimed in claim 3, wherein the desiccant used is a molecular sieve or silica gel.

* * * * *